US005618563A

United States Patent [19]
Berde et al.

[11] Patent Number: 5,618,563
[45] Date of Patent: Apr. 8, 1997

[54] BIODEGRADABLE POLYMER MATRICES FOR SUSTAINED DELIVERY OF LOCAL ANESTHETIC AGENTS

[75] Inventors: Charles B. Berde, Brookline; Robert S. Langer, Newton, both of Mass.

[73] Assignee: Children's Medical Center Corporation, Boston, Mass.

[21] Appl. No.: 119,958

[22] Filed: Sep. 10, 1993

Related U.S. Application Data

[63] Continuation-in-part of Ser. No. 943,287, Sep. 10, 1992, abandoned.

[51] Int. Cl.⁶ .................................................. A61K 9/16
[52] U.S. Cl. .......................... 424/501; 424/499; 514/818
[58] Field of Search ...................... 424/484, 486, 424/488, 499, 501, 465, 468, 456, 422–423, 490; 514/772.7; 264/DIG. 65, 12, 13, 301, 309, 322; 425/DIG. 245

[56] References Cited

U.S. PATENT DOCUMENTS

| | | | |
|---|---|---|---|
| 3,185,625 | 5/1965 | Brown | 167/82 |
| 3,755,558 | 8/1973 | Scribner | 424/47 |
| 3,972,995 | 8/1976 | Tsuk et al. | 424/28 |
| 4,034,758 | 7/1977 | Theeuwes | 128/260 |
| 4,039,653 | 8/1977 | DeFoney et al. | 424/19 |
| 4,059,686 | 11/1977 | Tanaka et al. | 424/19 |
| 4,070,347 | 1/1978 | Schmitt | 260/77.5 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,226,848 | 10/1980 | Nagai et al. | 424/19 |
| 4,250,163 | 2/1981 | Nagai et al. | 424/14 |
| 4,369,172 | 1/1983 | Schor et al. | 424/19 |
| 4,434,153 | 2/1984 | Urquhart et al. | 424/22 |
| 4,530,840 | 7/1985 | Tice et al. | 514/179 |
| 4,542,025 | 9/1985 | Tice et al. | 424/78 |
| 4,568,535 | 2/1986 | Loesche | 424/19 |
| 4,568,536 | 2/1986 | Kronenthal et al. | 424/22 |
| 4,569,837 | 2/1986 | Suzuki et al. | 424/28 |
| 4,585,651 | 4/1986 | Beck et al. | 424/88 |
| 4,591,496 | 5/1986 | Cohen et al. | 424/15 |
| 4,597,960 | 7/1986 | Cohen | 424/28 |
| 4,622,244 | 11/1986 | Lapka et al. | 427/213.32 |
| 4,638,045 | 1/1987 | Kohn et al. | 530/323 |
| 4,650,665 | 3/1987 | Kronenthal et al. | 424/435 |
| 4,652,441 | 3/1987 | Okada et al. | 424/19 |
| 4,685,883 | 8/1987 | Jernberg | 433/215 |
| 4,713,244 | 12/1987 | Bawa et al. | 424/429 |

(List continued on next page.)

FOREIGN PATENT DOCUMENTS

| | | |
|---|---|---|
| 0195906 | 2/1986 | European Pat. Off. ........ A61K 31/71 |
| 0244118 | 4/1987 | European Pat. Off. ......... A61K 9/10 |
| WO91/17772 | 11/1991 | WIPO ............................ A61K 47/30 |
| WO92/07555 | 5/1992 | WIPO ............................ A61K 9/22 |
| WO93/20138 | 10/1993 | WIPO . |
| WO95/09613 | 4/1995 | WIPO . |

OTHER PUBLICATIONS

Leong K. et al., Bioerodable Polyanhydride as Drug–carrier Matrices. I: Characterization, Degradation, and Release Characteristics, *Journal of Biomedical Materials Research* 19:941–955 (1985).

(List continued on next page.)

*Primary Examiner*—Edward J. Webman
*Attorney, Agent, or Firm*—Arnall Golden & Gregory

[57] ABSTRACT

An improved biodegradable controlled release system consisting of a polymeric matrix incorporating a local anesthetic for the prolonged administration of the local anesthetic agent, and a method for the manufacture thereof, are disclosed. The polymers and method of manufacture used to form the PLAMs are selected on the basis of their degradation profiles: release of the topical anesthetic in a linear, controlled manner over a period of preferably two weeks and degradation in vivo with a half-life of less than six months, more preferably two weeks, to avoid localized inflammation. Alternatively, a non-inflammatory can be incorporated into the polymer with the local anesthetic to prevent inflammation.

7 Claims, 9 Drawing Sheets

U.S. PATENT DOCUMENTS

| | | | |
|---|---|---|---|
| 4,732,155 | 3/1988 | Zetter et al. | 128/630 |
| 4,735,945 | 4/1988 | Sakamoto et al. | 514/279 |
| 4,753,652 | 6/1988 | Langer et al. | 623/1 |
| 4,757,128 | 7/1988 | Domb et al. | 528/271 |
| 4,779,806 | 10/1988 | Langer et al. | 241/1 |
| 4,780,320 | 10/1988 | Baker | 424/493 |
| 4,789,724 | 12/1988 | Domb et al. | 528/176 |
| 4,806,621 | 2/1989 | Kohn et al. | 528/211 |
| 4,857,311 | 8/1989 | Domb et al. | 424/78 |
| 4,861,627 | 8/1989 | Mathiowitz et al. | 427/213.31 |
| 4,863,735 | 9/1989 | Kohn et al. | 424/422 |
| 4,886,870 | 12/1989 | D'Amore et al. | 528/206 |
| 4,891,225 | 1/1990 | Langer et al. | 424/428 |
| 4,898,734 | 2/1990 | Mathiowitz et al. | 424/426 |
| 4,900,556 | 2/1990 | Wheatley et al. | 424/450 |
| 4,906,474 | 3/1990 | Langer et al. | 424/428 |
| 4,916,204 | 4/1990 | Domb et al. | 528/271 |
| 4,919,939 | 4/1990 | Baker | 424/493 |
| 4,921,737 | 5/1990 | Wheatley et al. | 428/402.2 |
| 4,933,185 | 6/1990 | Wheatley et al. | 424/461 |
| 4,933,431 | 6/1990 | Domb et al. | 528/328 |
| 4,946,929 | 8/1990 | D'Amore et al. | 528/206 |
| 5,075,109 | 12/1991 | Tice et al. | 424/88 |
| 5,122,367 | 6/1992 | Ron et al. | 242/80 |
| 5,188,837 | 2/1993 | Domb | 424/450 |
| 5,227,165 | 7/1993 | Domb et al. | 424/450 |

OTHER PUBLICATIONS

Conix A. Poly [1,3-bis(p-carboxyphenoxy) propane anhydride], *Macro. Snyth.* 2:95–98 (1966).

Brown L. et al., Controlled Release of Insulin from Polymer Matrices: Control of Diabetes in Rats, *Diabetes* 35:692–697 (1987).

Brem H. et al., Interstiatial Chemotherapy with rug Polymer Implants for the Treatment of Recurrent Gliomas, *Journal of Neurosurgery* 74:441–446 (1986).

Brem H. et al., Biocompatability of a Biodegradable Controlled–release Polymer in the Rabbit Brain. *Sel Cancer Ther* 5(2):55–65 (1989).

Sharon C. et al., *Development of Drug Delivery Systems for Use in Treatment of Narcotic Addiction, Naltrexone: Research Monograph* 28, Edited by Willette RE, Barnette G. Nat. Institute on Drug Abuse, 194–213 (1980).

Langer R., New Methods of Drug Delivery, *Science*, 228:190 (1985).

Williams D.L. et al., "Microencapsulated Local Anesthetics," *Proc. Int. Symp. Rel. Bioact. Mater.* 11:69–70 (1984).

Devor, et al., *Pain* 22, 127–137 (1985).

Johansson, et al., *Acta Anaesthesiol. Scand.* 34, 335–338 (1990).

Waldman, et al., *J. Pain Symptom Management* 3(1), 39–43 (1988) (see in particular p. 42, column 2).

Glasser, et al., *J. Neurosurg.* 78, 383–387 (1993).

Guttu, et al., "Delayed Healing of Muscle After Injection of Bupivicaine and Steroid".

Flanagan, et al., *Ann. Royal Coll. Surg. Eng.* 70, 156–157 (1988).

Duncan, et al., "Treatment of Upper Extremity Reflex Sympathetic Dystrophy with Joint Stiffness Using Sympatholytic Bier Blocks and Manipulation" *Orthopedics* 11(6), 883–886 (1988).

Hall, et al., *Brain Research* 240, 186–190 (1982).

Sandrock and Warfield, "Epidural Steroids and Facet Injections" Ch. 29 *Principles and Practice of Pain Management* Warfield, C.A., editor (McGraw–Hill, Inc 1993).

"Avenues for the Medical Control of Abnormal Neural Discharge" *Textbook of Pain* Wall and Melzack (Churchill Livingstone 1994).

Bonica, John J. and F. Peter Buckley, "Regional Analgesia with Local Anesthetics," *The Management of Pain* II:1883–1966 (1990), Lea & Febiger (Eds.) Second Edition.

Devor, Marshall, et al., "Corticosteroids Suppress Ectopic Neural Discharge Originating in Experimental Neuromas," *Pain* 22:127–137 (1985).

McCleane, G., et al., "The addition of triamcinoione acetonide to bupivacaine has no effect on the quality of analgesia produced by ilioinguinal nerve block," *Anaesthesia* 4:819–820 (1994).

Anderson, J.M., et al., "The role of the fibrous capsule in the function of implanted drug–polymer sustained released systems," *J. Biomed. Mater. Res.*, 15, 889–902 (1981).

Berde, C.B., et al., Abstracts of Scientific Papers, 1990 Annual Meeting, Amer. Soc. Anesthesiologists, 73:A776 (Sep. 1990).

Christenson, L., et al., "Mast cells and tissue reaction to intraperitoneally implanted polymer capsules," *J. Biomed. Mater. Res.*, 25, 1119–1131 (1991).

Christenson, L., et al., "Tissue reaction to intraperitoneal polymer implants: Species difference and effects of corticoid and doxorubicin," *J. Biomed. Mater. Res.*, 23, 705–718 (1989).

Haynes, Duncan H., et al., "Ultra–long–duration Local Anesthesia Produced by Injection of Lecithin–coated Methoxyflurane Microdroplets," *Anesthesiology* 63:490–499 (1985).

Iannotti, J.P., et al., "Synthesis and Characterization of Magnetically Responsive Albumin Microspheres Containing cis–Hydroxyproline for Scar Inhibition," *Orthop. Res. Soc.*, 9, 432–444 (1991).

Ingbar, Donald and Judah Folkman, "Inhibition of Angiogenesis Through Modulation of Collagen Metabolism," *Lab. Invest.*, 59, 44–51 (1988).

Ksander, George A., et al, "Experimental effects on surrounding fibrous capsule formation from placing steroid in a silicone bag–gel prosthesis before implantation," *Plast. & Reconstr. Surg.*, 62, 873–883 (1978).

Lewis, D.H., et al., "The Use of In Vitro Release Methods to Guide the Development of Controlled–Release Formulations," 9th International Symposium on Controlled Release of Bioactive Materials, Sponsored by Controlled Release Society, Inc.

Martyn, J.A.J., et al., "Up–and–down Regulation of Skeletal Muscle Acetylcholine Receptors," *Anesthesiology* 76:822–843 (1992).

Masters, D.B., et al., Meeting for the American Society of Anesthesiologists 75:A680 (1991).

Masters, David B., et al, "High Sensitivity Quantification of RNA from Gels and Autoradiograms with Affordable Optical Scanning," *BioTechniques* 12:902–911 (1992).

Masters, D.B., et al., "Prolonged Sciatic Nerve Blockage Using Sustained Release of Veratridine from a Biodegradable Polymer Matrix," *Soc. Neurosci. Abstr.* 18:200 (1992).

Schneider, Markus, et al., "A Preferential Inhibition of Impulses in C–fibers of the Rabbit Vagus Nerve by Veratridine an Activator of Sodium Channels," *Anesthesiology* 74:270–281 (1991).

Terranova, Victor, P., et al., "Biochemically mediated periodontal regeneration," 248.

Tice, Thomas R., et al., "Controlled Release of Ampicillin and Gentamicin From Biodegradable Microcapsules," 108–111.

Tice, T.R., et al., "Development of Microencapsulated Antibiotics for Topical Administration," 168–170.

Too, Heng–Phon and John E. Maggio, "Radioimmunoassay of Tachykinins," *Methods in Neurosciences,* edited by Conn PM, New York, Academic Press, 1991, pp. 232–247.

Wakiyama, Naoki, et al., "Preparation and Evaluation in Vitro and in Vivo og Polylactic Acid Microspheres containing Dibucaine," *Chem. Pharm. Bull.* 30:3719–3727 (1982).

Wakiyama, Naoki, et al., "Influence of Physicochemical Properties of Polylactic Acid on the Characteristics and in Vitro Release Patterns of Polyactic Acid Microspheres containing Local Anesthetics," *Chem. Pharm. Bull.* 30:2621–2626 (1982).

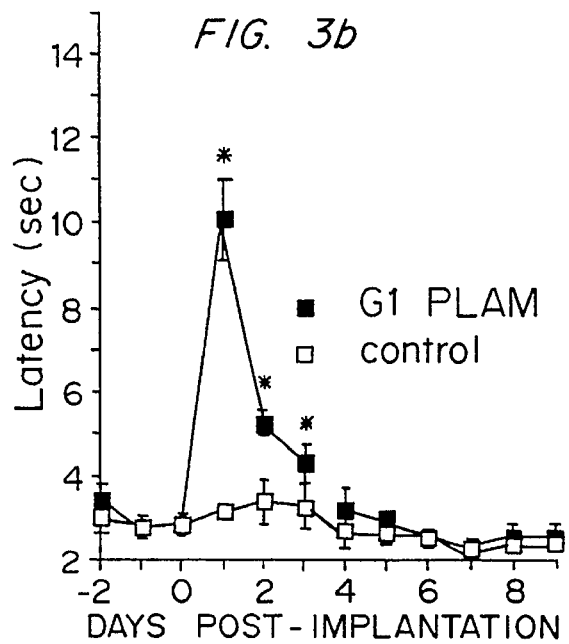
FIG. 3b
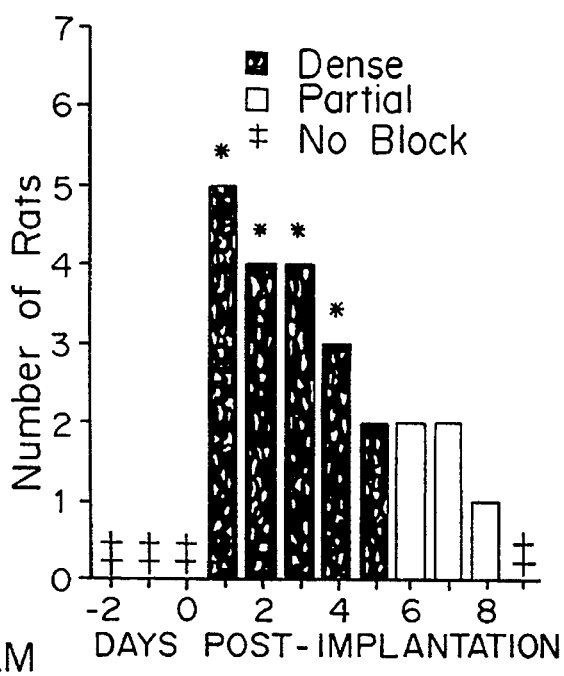
FIG. 3c
FIG. 3d

BIODEGRADABLE POLYMER MATRICES FOR SUSTAINED DELIVERY OF LOCAL ANESTHETIC AGENTS

The U.S. Government has rights in this invention pursuant to National Institutes of Health Grant No. GM-15904 to Harvard Anesthesia Research and Teaching Center to C. Berde, and Grant No. CA 5257 to R. Langer.

This is a continuation-in-part of U.S. Ser. No. 07/943,287, filed Sep. 10, 1992 now abandoned by Charles B. Berde and Robert S. Langer.

BACKGROUND OF THE INVENTION

This invention is generally in the field of anesthesiology and, in particular, the delivery of anesthetic agents which locally block pain for periods of time of less than about two weeks.

In order to provide local or regional blockade for extended periods, clinicians currently use local anesthetics administered through a catheter or syringe to a site where the pain is to be blocked. This requires repeated administration where the pain is to be blocked over a period of greater than one day, either as a bolus or through an indwelling catheter connected to an infusion pump. These methods have the disadvantage of potentially causing irreversible damage to nerves or surrounding tissues due to fluctuations in concentration and high levels of anesthetic. In addition, anesthetic administered by these methods are generally neither confined to the target area, nor delivered in a linear, continuous manner. In all cases, analgesia rarely lasts for longer than six to twelve hours, more typically four to six hours. In the case of a pump, the infusion lines are difficult to position and secure, the patient has limited, encumbered mobility and, when the patient is a small child or mentally impaired, may accidentally disengage the pump.

Drugs are typically administered in a variety of ways, including by injection, topical administration, oral ingestion, and sustained release devices. Methods which provide for systemic, rather than localized, delivery are not an option with local anesthetics since these could interfere with the patient's ability to breathe, if administered systemically. Devices could potentially provide for a sustained, controlled, constant localized release for longer periods of time than can be achieved by injection or topical administration. These devices typically consist of a polymeric matrix or liposome from which drug is released by diffusion and/or degradation of the matrix. The release pattern is usually principally determined by the matrix material, as well as by the percent loading, method of manufacture, type of drug being administered and type of device, for example, microsphere. A major advantage of a biodegradable controlled release system over others is that it does not require the surgical removal of the drug depleted device, which is slowly degraded and absorbed by the patient's body, and ultimately cleared along with other soluble metabolic waste products.

Systemic anesthetics such as methoxyflurane, have been incorporated into liposomes and lecithin microdroplets, for example, as described by Haynes, et al., *Anesthesiology* 63: 490–499 (1985). To date, the liposome and lecithin preparations have not been widely applied in clinical or laboratory practice, because of their inability to provide dense blockade for a prolonged period of time (i.e., three or more days) in a safe and controlled manner. The lecithin microdroplets and liposomes degrade or are phagocytized too rapidly, in a matter of hours. Other lipid based devices, formed in combination with polymer, for release of local anesthetics are described by U.S. Pat. No. 5,188,837 to Domb.

Local anesthetics have been incorporated into biodegradable polymeric devices, for example, polylactic acid microspheres, as described by Wakiyama, et al., *Chem. Pharm. Bull.*, 30: 3719–3727 (1982). In contrast to the lipid based materials, the poly(lactic acid) devices take over a year to degrade and cause localized inflammation. Berde, et al., Abstracts of Scientific Papers, 1990 Annual Meeting, Amer. Soc. Anesthesiologists, 73: A776 (Sep. 1990), reported the use of a device formed of a polyanhydride polymer matrix of copolymer 1,3 bis (p-carboxyphenoxy)propane and sebacic acid, in a ratio of 1:4, into which dibucaine free base was incorporated by compression molding. This drug-polymer device, however, had several drawbacks. For example, because the drug was incorporated into the polymer matrix by compression molding, the device sometimes displayed bulk erosion, causing fast initial release of drug. In addition, the device often generated an inflammatory response or a capsule of serous material or fibrin, which is particularly a problem when located adjacent to nerves.

Accordingly, it is the object of this invention to provide an improved biodegradable controlled release device which administers local anesthetic for a prolonged period of time in a substantially constant, linear fashion and which provokes minimal encapsulation and/or other immune responses.

It is a further object of the present invention to provide a method and means for modulating the rate of release of the local anesthetic from the bioerodible polymer matrix.

SUMMARY OF THE INVENTION

An improved biodegradable controlled release device for the prolonged administration of a local anesthetic agent, and a method for the manufacture thereof are disclosed. The device is formed of a biodegradable polymer degrading significantly within a month, with at least 50% of the polymer degrading into non-toxic residues which are removed by the body within a two week period. Useful polymers include polyanhydrides, polylactic acid-glycolic acid copolymers and polyorthoesters containing a catalyst. Local anesthetics are incorporated into the polymer using a method that yields a uniform dispersion, such as melt casting or spray drying, not compression molding. Local inflammatory responses against the polymeric devices are avoided through selection of the polymer, repeated recrystallization of the monomers forming the polymer and resulting polymers to remove impurities, monomer and degradation products, the method of incorporation of the anesthetic and in some embodiments, by inclusion of an antiinflammatory such as dexamethasone, either within the polymer or implanted with the polymer. The device can be formed as slabs, films, microparticles, including microspheres, or a paste.

The type of anesthetic and the quantity are selected based on the known pharmaceutical properties of these compounds. It has been discovered that bupivacaine is a better anesthetic agent for use in polymeric devices than other local anesthetics such as dibucaine. It has also been determined that salts of the anesthetic agents (e.g., hydrochlorides, bromides, acetates, citrates, sulfates, etc.) yield better results when incorporated into polymeric devices than the free base forms.

It is possible to tailor a device to deliver a specified initial dosage and subsequent maintenance dose by manipulating the percent drug incorporated, the form of local anesthetic, for example, more hydrophobic free base versus more hydrophilic hydrochloride, the method of production, and the shape of the matrix.

The polymeric devices are implanted at the site where the anesthetic is to be released. This can be at the time of surgery, prior to or at the time of injection, especially when the device is in the form of microparticles, or following removal of systemic anesthetic.

Examples demonstrate the superiority of making the polymeric device using a method resulting in uniform dispersion of anesthetic in the device and prevention of inflammation by incorporation of an antiinflammatory with the anesthetic-polymeric device. The device delivers the local anesthetic at rates above 3.5 mg/day for up to four days or more with substantially zero order kinetics, i.e., linear release. The effectiveness of these devices in vivo is also demonstrated. Using a rat sciatic nerve in vivo model, it was shown that the devices provide degrees of sensory blockade for up to five to six days and motor blockade for up to three days. The blockade appeared reversible, with complete recovery of strength and sensation.

The examples also demonstrate the effect of cis-hydroxyproline and dexamethasone on inflammation, encapsulation and duration of sensory and motor blockade following implantation of bupivacaine 20% CPP:SA (20:80) polymer matrices along the sciatic nerves of rats. Cis-hydroxyproline (CHP) did not diminish encapsulation and did not alter the duration of sensory or motor blockade. In contrast, dexamethasone (DMS) produced significant reductions in encapsulation and inflammation, and was associated with more prolonged sensory analgesia. These effects were not mediated by systemic concentrations of dexamethasone, since unilateral incorporation of DMS into PLAM did not diminish encapsulation around contralateral control implants that did not receive DMS. DMS was effective in inhibiting an anti-inflammatory response and preventing encapsulation of the polymeric device in rats at doses from 45 µg to 180 µg, administered in three pellets containing between 15 µg and 60 µg DMS/pellet. The preferred dosage is 60 µg anti-inflammatory/kg body weight, which is equivalent to a dosage range of between 20 µg/kg body weight, and 1 mg/kg body weight. These doses did not produce suppression of glucocorticoid secretion.

BRIEF DESCRIPTION OF THE DRAWINGS

FIGS. 3a–3f are graphs of the results of nerve block assays: FIG. 3a is a graph of the number of rats over days post-implantation showing dense, partial or no block pain relief; FIG. 3b is a graph of latency in seconds over days post-implantation for G1 devices (dark squares) and control (open squares); FIG. 3c is a graph of the number of rats showing dense, partial or no block pain relief over days post-implantation; FIG. 3d is a graph of latency in seconds over days post-implantation for G2 devices (dark circles) and control (open circles); FIG. 3e is a graph of the number of rats showing dense, partial or no block pain relief over days post-implantation; and FIG. 3f is a graph of latency in seconds over days post-implantation for G3 devices (dark circles) and control (open circles). The data represent mean ±S.E.M. *Denotes $p<0.05$ significance(†, $p=0.07$).

DETAILED DESCRIPTION OF THE INVENTION

Figure 1A:
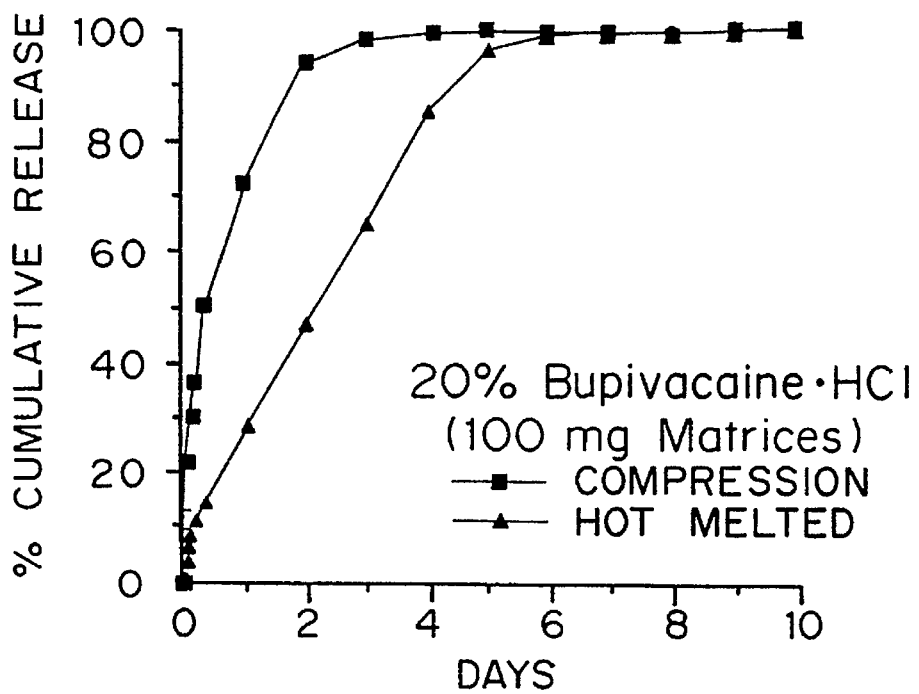
FIGS. 1a and 1b are graphs of the percent cumulative release of bupivacaine HCl (FIG. 1a) and dibucaine HCl (FIG. 1b) as a function of time in days, comparing release from hot melt molded devices with release from compression molded devices formed of 1,3 bis (p-carboxyphenoxy)propane:sebacic acid (CPP:SA) (1:4).

Systems for the controlled and prolonged delivery of a local anesthetic agent to a targeted area are provided. These systems can be used for the management of various forms of persistent pain, such as postoperative pain, sympathetically maintained pain, or certain forms of chronic pain such as the pain associated with many types of cancer.

Polymers

It is important that the polymer degrade in vivo over a period of less than a year, with at least 50% of the polymer degrading within six months or less. More preferably, the polymer will degrade significantly within a month, with at least 50% of the polymer degrading into non-toxic residues which are removed by the body, and 100% of the drug being released within a two week period. Polymers should also degrade by hydrolysis by surface erosion, rather than by bulk erosion, so that release is not only sustained but also linear. Polymers which meet this criteria include some of the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid. Polylactic acid is not useful since it takes at least one year to degrade in vivo.

The local anesthetic is present in the polymer at a concentration effective to achieve nerve blockade at the site of administration.

The polymers should be biocompatible. Biocompatibility is enhanced by recrystallization of either the monomers forming the polymer and/or the polymer using standard techniques.

Anesthetics

The systems employ biodegradable polymer matrices which provide controlled release of local anesthetics. As used herein, the term "local anesthetic" means a drug which provides local numbness or pain relief. A number of different local anesthetics can be used, including dibucaine, bupivacaine, etidocaine, tetracaine, lidocaine, and xylocaine. The preferred anesthetic is bupivacaine or dibucaine, most preferably in the form of a salt, for example, the hydrochloride, bromide, acetate, citrate, or sulfate. Compared to the free base form of these drugs, the more hydrophilic hydrochloride salt displays longer and denser nerve block, more complete release from polymer matrices, slower clearance from the targeted nerve area, and less encapsulation. Bupivacaine is a particularly long acting and potent local anesthetic when incorporated into a PLAM. Its other advantages include sufficient sensory anesthesia without significant motor blockage, lower toxicity, and wide availability.

The devices can also be used to administer local anesthetics that produce modality-specific blockade, as reported by Schneider, et al., *Anesthesiology,* 74: 270–281 (1991), or that possess physical-chemical attributes that make them more useful for sustained release then for single injection blockade, as reported by Masters, et al., *Soc. Neurosci. Abstr.,* 18: 200 (1992), the teachings of which are incorporated herein.

The anesthetic is incorporated into the polymer in a percent loading of 0.1% to 70% by weight, preferably 5% to 50% by weight. It is possible to tailor a system to deliver a specified loading and subsequent maintenance dose by manipulating the percent drug incorporated in the polymer and the shape of the matrix, in addition to the form of local anesthetic (free base versus salt) and the method of production. The amount of drug released per day increases proportionately with the percentage of drug incorporated into the matrix (for example, from 5 to 10 to 20%). In the preferred embodiment, polymer matrices with not more than about 30% drug incorporated are utilized, although it is possible to incorporate substantially more drug, depending on the drug, the method used for making and loading the device, and the polymer.

Antiinflammatories

Antiinflammatories that are useful include steroids such as dexamethasone, cortisone, prednisone, and others routinely administered orally or by injection. Useful loadings are from 1 to 30% by weight. The preferred dosage is 60 µg anti-inflammatory/kg body weight, which is equivalent to a dosage range of between 20 µg/kg body weight, and 1 mg/kg body weight.

The following examples demonstrate that polymers alone and when combined with local anesthetics generate a substantial encapsulation response within two weeks of placement in rats. The encapsulation response to polymer containing local anesthetic is worse than the polymer alone. This encapsulation is a natural response to a foreign body and occurs at varying rates with many substances commonly regarded as "biocompatible". Minimization of the encapsulation response is important for proper healing, for avoidance of unsightly scars, for optimal access of drug to its site of action, and potentially to decrease the likelihood of infection.

Encapsulation involves formation of a fibrous material around foreign bodies. It begins with attempts by granulocytes to phagocytose and incorporate the foreign material during the initial acute inflammatory response. The process of encapsulation through fibrosis is due to histiocytes and fibroblasts, which generate the layers of collagenous connective tissue surrounding the implant. Encapsulation depends upon several factors, including the chemical and physical characteristics of the implant, the mechanical action of the implant, its site in the body and the presence of microorganisms.

The examples demonstrate that dexamethasone reduces encapsulation, does not reduce the intensity of the nerve block generated by the release of anesthetic from the polymer, does not affect the recovery of sensation and strength, and works only locally due to the low doses which are effective, and therefore exerts no effect on the normal pituitary-adrenal hormone responses.

Methods of Manufacture

The polymeric devices are preferably manufactured using a method that evenly disperses the anesthetic throughout the device, such as solvent casting, spray drying or hot melt, rather than a method such as compression molding. As shown by Example 1, in contrast to compression molded tablets, which sometimes display bulk erosion and fast initial release of drug, hot melt molded tablets have denser and more homogenous matrices, causing them to release drug in a more safe and linear fashion.

The form of the polymeric matrix is also important. Devices can be shaped as slabs, beads, pellets, microparticles, including microspheres and microcapsules, or formed into a paste. Microparticles, microspheres, and microcapsules are collectively referred to herein as "microparticles". The device can be coated with another polymer or other material to alter release characteristics or enhance biocompatibility. The microparticles can be administered as a suspension or as a device within a gelatin capsule, or used to form a paste, for example.

In the preferred embodiments, the device will be in the form of microparticles. A desired release profile can be achieved by using a mixture of microparticles formed of polymers having different release rates, for example, polymers releasing in one day, three days, and one week, so that linear release is achieved even when each polymer per se does not release linearly over the same time period.

Methods of Administration

In the preferred method of administration, the devices are microparticles and are administered by injection at the site where pain relief is to be achieved. Alternatively, the device is surgically implanted at the site. The pellets may be injected through a trochar, or the pellets or slabs may be surgically placed adjacent to nerves.

Potential applications include two to five day intercostal blockade for thoracotomy, or longer term intercostal blockade for thoracic post-therapeutic neuralgia, lumbar sympathetic blockade for reflex sympathetic dystrophy, or three-day ilioinguinal/iliohypogastric blockade for hernia repair.

The present invention is further described with reference to the following non-limiting examples.

EXAMPLE 1

Preparation of Polymer Matrices for Sustained Release of Bupivacaine HCl

Monomers of CPP and SA (20:80) were converted to mixed anhydrides after a 30 minute reflux in acetic anhydride. The prepolymers were then recrystallized over several weeks in a mixed solvent of acetic anhydride and dimethylformamide, followed by polycondensation under nitrogen sweep. The resulting polymers were then ground to a fine powder and mixed with crystalline Bupivacaine HCL (20%±2% drug by dry weight). Cylindrical pellets were then produced by placing a tuberculin syringe filled with drug-polymer mixture in a dry oven at 115° C. for 15–20 min. and then injecting the molten solid into teflon tubing (3.2 mm i.d.) or by compression of the polymer powder.

Release of bupivacaine from the device was measured in phosphate buffer, pH 7.4, over a period of 10 days. The results comparing release from compression molded-tablets and hot melt-pellets are shown in FIG. 1a. Significantly more linear release was obtained with devices prepared by hot melt.

EXAMPLE 2

Preparation of Polymer Matrices for Sustained Release of Dibucaine

Figure 1B:
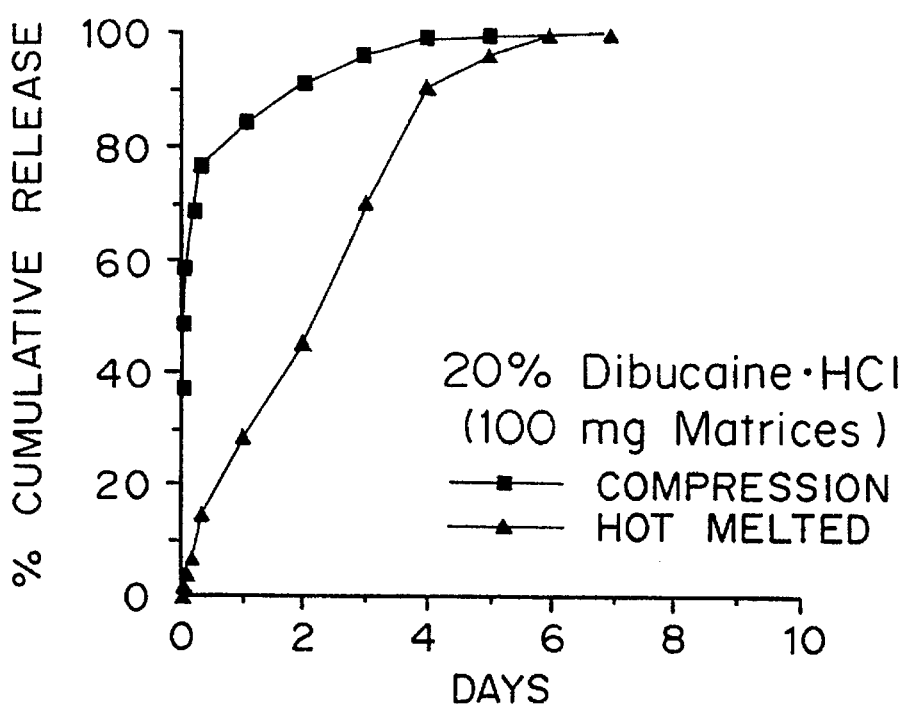

Polymer-drug matrices were prepared as detailed above, substituting crystalline dibucaine HCl for bupivacaine HCl. Release of dibucaine from matrices was then measured in phosphate buffer, pH 7.4, over a period of 10 days. The results comparing release from compression molded-tablets and hot melt-pellets are shown in FIG. 1b. The same release profiles were observed.

EXAMPLE 3

Prolonged Regional Nerve Blockade by Controlled Release of Local Anesthetic From a Biodegradable Polymeric Matrix Cylindrical pellets made from polymer matrices incorporated with bupivacaine-HCl were implanted surgically along the sciatic nerves of rats in vivo. Sensory and motor blockade was produced for periods ranging from two to six days. Contralateral control legs receiving polymer implants without drug showed no block. Blockade was reversible, and animals appeared to recover sensory and motor function normally. Biochemical indices of nerve and muscle function were indistinguishable from contralateral controls. This biodegradable polymer system provides a promising new alternative for the delivery of local anesthetics to peripheral nerves to produce prolonged blockage for the management of acute and chronic pain.

Methods and Materials
PLAM Implants

Biodegradable polymeric pellets were formed from a polymer mixture, 20% poly[bis(p-carboxyphenoxy) propane anhydride] (poly CPP) and 80% sebacic acid (SA), impregnated with crystalline bupivacaine·HCl, to release this local anesthetic in a controlled manner. Polymer-local anesthetic matrix (PLAM) pellets were made by mixing 150 µm sieved crystals of bupivacaine-HCl at 12% and 20% with polymer powder. In brief, cylindrical pellets were produced by melting the mixtures in a tuberculin syringe at 115° C. in a dry oven and then injecting the molten mixture into Teflon tubing (3.2 or 4.8 mm i.d.). After cooling, the pellets were cut to specified lengths and weights. Control pellets were made in an identical manner using polymer without drug.

Three sizes of PLAM pellets, loaded to 20% by weight with bupivacaine·HCl, were used as implants-to examine dosage effects. Group 1 pellets weighed 50±3 mg and were 4.0±0.3 mm long, 3.1±0.2 mm diameter. Group 2 pellets were twice the length of Group 1 pellets, 100±5 mg, 9.8±2 mm long and 3.1±0.2 diameter. Group 3 pellets weighed 125±5 mg and were 6.0±0.1 mm long, 4.7±0.2 mm diameter. Pellets were sterilized via gamma irradiation for in vitro or in vivo use. Different batches of PLAM pellets were used and similar results were obtained.

In Vitro

Bupivacaine PLAM pellets (equal in size to Group 2 pellets) loaded with 12% or 20% bupivacaine were immersed in various volumes (2 ml, 10 ml, 25 ml) of phosphate-buffered saline (PBS) with 0.1% sodium azide (pH 7.4 at 37° C.). Buffer was collected and replaced at 0.5, 2, 8, 16, 24 hour time points, then once daily thereafter for 3 weeks and stored at −20° C. before high performance liquid chromatography (HPLC) assay. Bupivacaine standards, 0.23, 0.46, 0.77, 2.3 µg, analyzed on average after every tenth sample, produced linear response values ($R^2$>0.995).

PLAM Implantation

For surgery, male rats (150–250 g Sprague-Dawley) were anesthetized with 50–75 mg/kg pentobarbital (i.p.) for Groups 1 and 2 and halothane for Group 3 (4% in oxygen for induction and 2% for maintenance). The shaved skin of the dorsal thigh was incised midway between the hip and the knee. The hamstring muscles were divided with a small hemostat, exposing the dorsal aspect of the sciatic nerve. Under direct vision, polymer pellets could be easily fitted into a large space between muscle layers surrounding the nerve. The space containing the pellets was bathed with 0.5 cc of an antibiotic solution (5000 units/ml penicillin G sodium and 5000 µg/ml streptomycin sulfate). The fascia overlaying the hamstrings were reapproximated with a single suture before closing skin with two wound clips.

For all rats, PLAM pellets were implanted surgically along the sciatic nerve in the upper thigh, with drug-containing implants on the experimental side and control (drug-free) implants on the contralateral (control) side.

Nerve Block Tests
Motor Block

The rats were behaviorally tested for sensory and motor blockage in a quiet observation room at 24°±1° C. PLAM implantation was only performed in rats showing appropriate baseline hot plate latencies after at least one week of testing. In all testing conditions, the experimenter recording the behavior was unaware of the side containing the local anesthetic. To assess motor block, a 4-point scale based on visual observation was devised: (1) normal appearance, (2) intact dorsiflexion of foot with an impaired ability to splay toes when elevated by the tail, (3) toes and foot remained plantar flexed with no splaying ability, and (4) loss of dorsiflexion, flexion of toes, and impairment-of gait. For graphing clarity, partial motor block equals a score of 2 and dense motor block is a score of either 3 or 4.

Sensory Block

Sensory blockade was measured by the time required for each rat to withdraw its hind paw from a 56° C. plate (IITC Life Science Instruments, Model 35-D, Woodland Hills, CA). The rats were held with a cloth gently wrapped above their waist to restrain the upper extremities and obstruct vision. The rats were positioned to stand with one hind paw on a hot plate and the other on a room temperature plate. With a computer data collection system (Apple IIe with a footpad switch), latency to withdraw each hind paw to the hot plate was recorded by alternating paws and allowing at least fifteen seconds of recovery between each measurement. If no withdrawal occurred from the hot plate within 15 seconds for Groups 1 and 2 or 12 sec for Group 3, the trial was terminated to prevent injury and the termination time was recorded. Testing ended after five measurements per side, the high and low points were disregarded, and the mean of the remaining three points was calculated for each side. Animals were handled in accordance with institutional, state and federal guidelines.

Necropsy

The animals were sacrificed two weeks after implantation, approximately one week after they all returned to baseline levels in motor and sensory tests. In vitro approximations predict drug depletion (<5% left) from the polymer matrix by one week, corresponding well with the observed block. Thus, the sciatic nerve was free of local anesthetic for approximately one week before postmortem analyses.

Histology

Sections of sciatic nerve approximately 2–3 cm in length, adjacent and proximal to the implants, were preserved in 10% formalin solution (24 mM sodium phosphate, pH 7). Sections were then embedded in paraffin, stained with hematoxylin and eosin, and examined by light microscopy.

Plasma Analysis

Five rats (250–275 g), anesthetized with ketamine-HCl (100 mg/ml at 1.5 ml/kg, i.p.) and xylazine (4 mg/ml at 4 mg/kg, i.p.), were implanted with a silastic catheter into the right jugular vein. Two days after the catheters were implanted, Group 1 pellets loaded with 20% bupivacaine (300 mg) were implanted next to the sciatic nerve. Blood was withdrawn (0.5 cc) before implantation and 1, 4, 24, 48, 72, and 96 hours after PLAM implantation via the indwelling central venous cannulae. Plasma was extracted with an equal volume of HPLC grade methanol (Fischer Scientific, Pittsburgh, Penn.), centrifuged (10,000×g) and the methanol phase filtered (0.2 μm nylon syringe type, Rainin, Woburn, Mass.) prior to HPLC analysis. The HPLC reliably quantified bupivacaine concentrations in the plasma methanol extraction phase down to 10 ng/ml. The bupivacaine standards used for blood plasma analyses were added to plasma aliquots prior to methanol extraction. The peak matching the standard bupivacaine peak's retention time was verified in plasma samples by doping with bupivacaine.

Biochemical Assays

Acetylcholine Receptor

The gastrocnemius muscle was excised from rats that had received group 2 implants and assayed for $I_{125}$ alpha-bungarotoxin binding as described by Martyn et al., *Anesthesiology* 76: 822–843, 1992; and Masters et al. Meeting for the American Society of Anesthesiologists 75: A680, 1991. Gastrocnemius muscle $I^{125}$ alpha-bungarotoxin binding was used as a measure of acetylcholine receptor number, which up-regulate (increase) in response to denervation.

Substance P and its Encoding mRNA

Ganglia were excised from cervical (C3-5) and lumbar (L4-6) regions, immediately frozen on dry ice and homogenized in a 3M lithium chloride/5M urea solution. The spun-down pellets were purified for RNA analysis by the method of Masters, et al., *BioTechniques*, 12: 902–911, 1992, and the supernatants were desalted on C-18 columns for peptide radioimmunoassay (RIA). In the RIA, unlabeled substance P was competed against Bolten-Hunger $I^{125}$ labeled substance P with a polyclonal antibody specific for substance P in duplicate samples, as described by Too H-P, Maggio J: Radioimmunoassay of Tachykinins, Methods in Neurosciences. Edited by Conn PM. New York, Academic Press, 1991, pp 232–247. The assay was sensitive to 5–10 femtomoles/assay tube. Protein levels eluted with substance P were analyzed with a microtiter plate bicinchoninic (BCA) protein assay (Pierce, Rockford, Ill.).

Northern blot analysis of dorsal root ganglia, able to accurately detect 20% differences in RNA levels in single dorsal root ganglia, was developed as described by Masters (1992). Purified total RNA samples were quantitated with an ethidium bromide Tris-acetate/EDTA gel and equal amounts loaded onto a formaldehyde denatured Northern gel. Relative quantities of messenger RNA encoding for the neuropeptide substance P were normalized to 28S ribosomal RNA (gamma-preprotachykinin/28S rRNA autoradiography grayscale density). Ethidium bromide photonegatives and hybridization autoradiograms were digitized with a flatbed optical scanner and the resulting image analyzed for grayscale density of the signal bands.

The Northern analysis used a full length cDNA of Y-preprotachykinin provided by Dr. J. Krause, Washington University, St. Louis, Mo. and subcloned into a Promega (Madison, Wis.) pGEM-3Z riboprobe vector. $^{32}$P-UTP labeled riboprobe (specific activity of approximately $10^9$ cpm/μg) was made using RNA T7-polymerase (Promega Piscataway, NJ). A 30-mer oligonucleotide sequence, complementary to a region of rat 28S ribosomal RNA (5'-AAUCCUGCUC AGUACGAGAG GAACCGCAGG-3'), was for normalization of total RNA loaded into the electrophoretic gel. Twenty ng of oligonucleotide was np end-labeled with the given procedure using T4 polynucleotide kinase (GIBCO BRL; Gaithersburg, Md.) and purified on a Nick size exclusion column. The specific activity of the probe was greatly reduced (to approximately $10^5$ cpm/μg) by adding 4 μg unlabeled oligonucleotide to the column eluent (400 μl) to reduce the hybridization signal and improve hybridization kinetics.

Statistics

Data were analyzed using linear regression tests, ANOVA, Chi Square tests and Wilcoxon rank-sum tests, where appropriate.

Results

In Vitro Release

Figure 2:
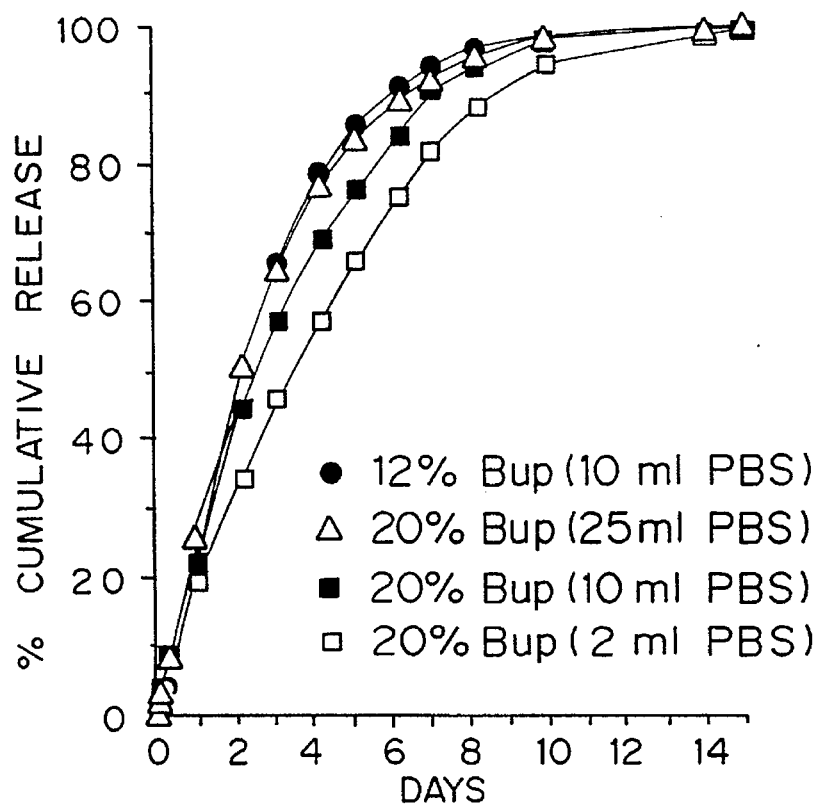
FIG. 2 is a graph of in vitro polymeric pellet release studies, percent cumulative release over time in days of 12% bupivacaine HCl in 10 ml PBS (dark circles); 20% bupivacaine HCl in 25 ml PBS (open triangles); 20% bupivacaine 10 ml PBS (dark squares); and 20% bupivacaine in 2 ml PBS (open square).

HPLC results showed that 96% of the 20 mg of bupivacaine incorporated into a 100 mg PLAM pellet was released within 8 days. Because release rate decreased with time, cumulative release rose toward an asymptote. The cumulative release profile was similar for 12% bupivacaine pellets in 10 ml buffer. Group 2 pellets were found to release approximately 75% of the loaded bupivacaine within 4 days in vitro, as shown in FIG. 2.

In Vivo Neural Block Measurements

Figure 3A:
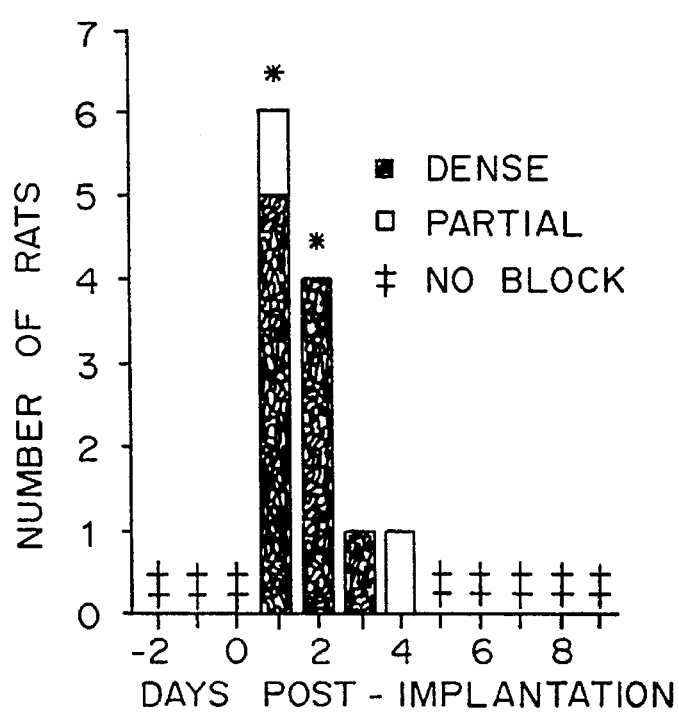
Figure 3E:
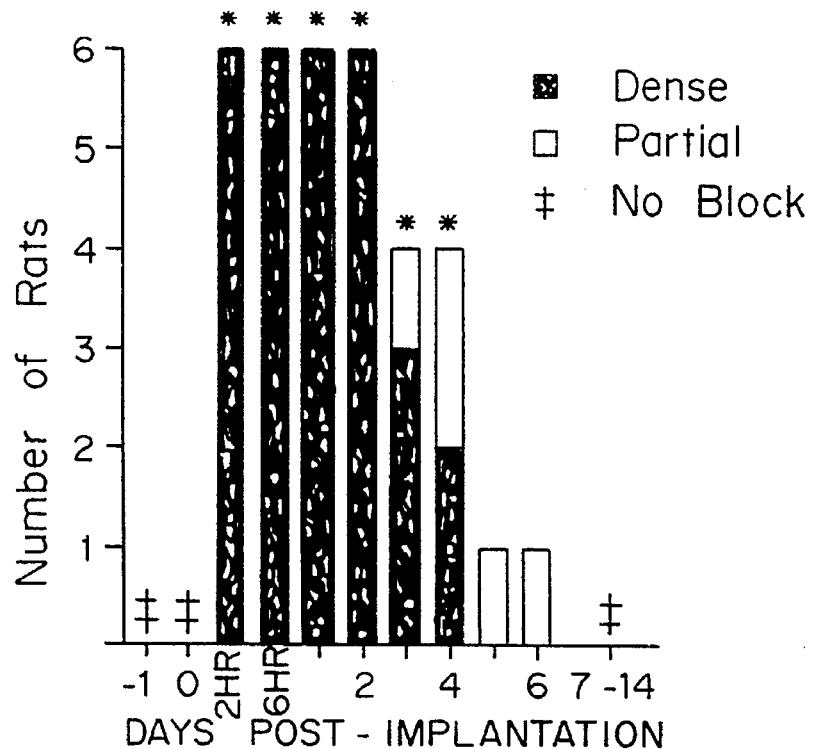
Figure 3F:
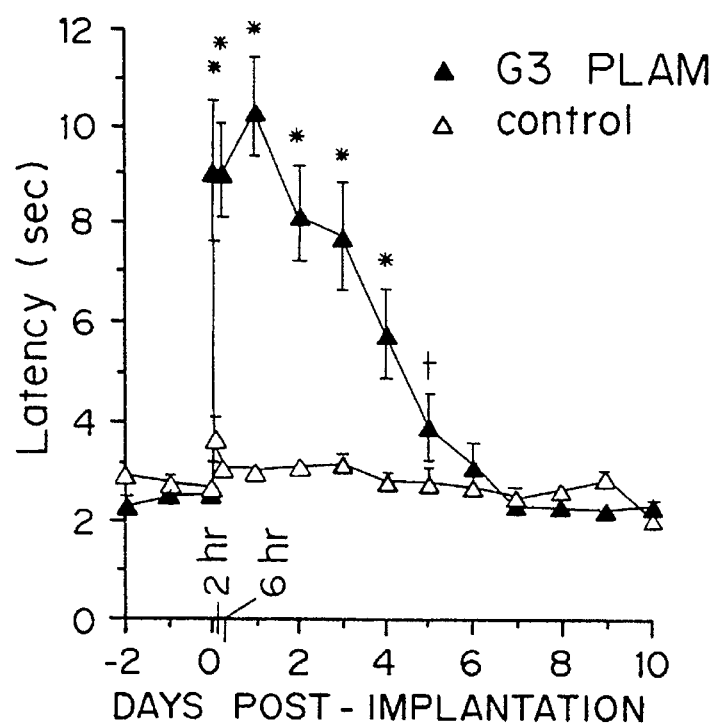

Group 1 implants (295±10 mg total PLAM) in seven animals produced sciatic nerve blockade for periods lasting 2–3 days, as shown in FIG. 3a. Dense motor blockade was evident in most animals for two days. Sensory blockade, measured as increased leg-withdrawal latency to heat in comparison to contralateral control leg, was greater than 200% for day 1 and greater than 70%–40% for days 2–3, respectively, as shown in FIG. 3b. Group 2 implants (295±10 mg total PLAM) in six animals produced sciatic nerve blockade for a 4 day period, as shown in FIG. 3c. Motor blockade was dense for 3–4 days in most animals. Sensory blockade increased leg-withdrawal latency greater than 200% for day 1, greater than 100% for day 2 and 3, and greater than 40% for day 4, as shown by FIG. 3d. One of the seven rats receiving a group 2 implant did not recover from the surgical implantation procedure. The animal appeared sluggish and lost weight, and was therefore dropped from the study. Group 3 implants (375±10 mg total PLAM) in six animals produced partial or complete motor blockade for 4 days and sensory blockade for 4–5 days, including leg-withdrawal latencies that increased over 185% for the first 3 days, greater than 100% for day 4 and greater than 30% for day 5, as shown by FIGS. 3e and 3f. No impairments were observed on the contralateral control side, implanted with an equal mass of polymer pellets without drug. These results indicate that the increased mass of the PLAM implant increases the period of blockade, suggesting a dose-response relationship.

Histology

Sciatic nerve histologic examination showed minimal perineural inflammation with a foreign body response consistent with a local response to previous surgery. Using light microscopy, no evidence of axonal degeneration or demyelination was noted either proximal or distal to the implantation site.

Biochemical Assays

Figure 4:
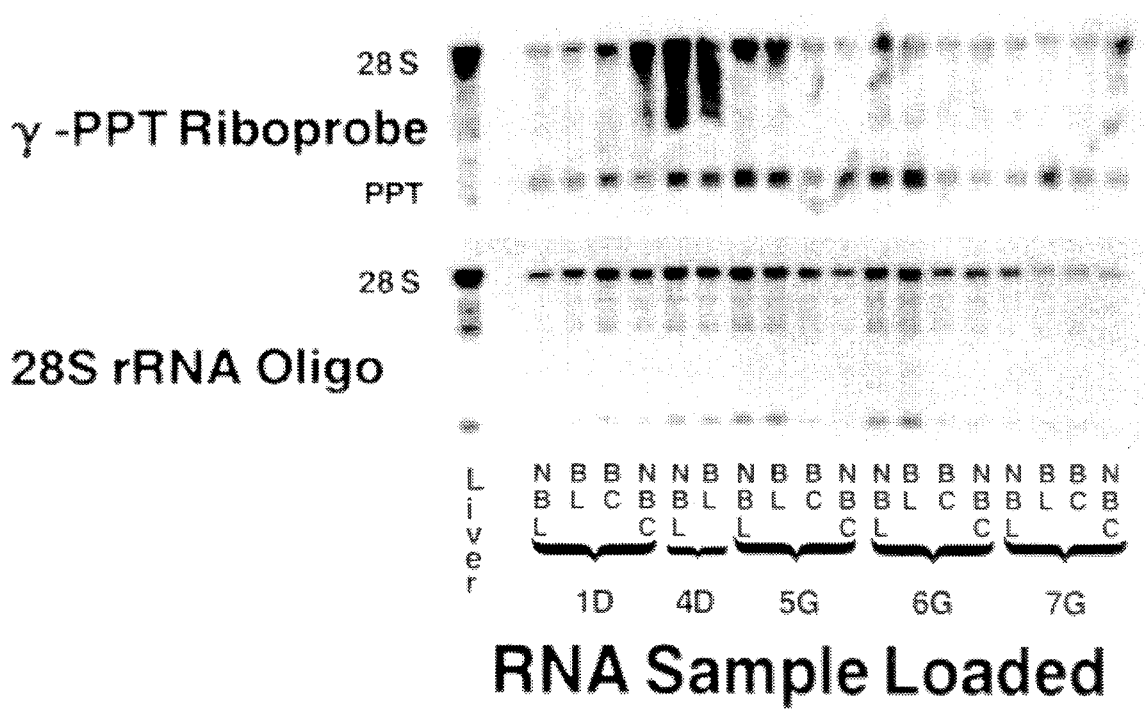
FIG. 4 is an autoradiogram of Northern blot analyses for five different rats receiving polymeric implants. This is an image of Northern autoradiograms that were digitized with an optical scanner for display and quantification. Radiolabeled probes were used to measure mRNA levels encoding substance P (preprotachykinin) extracted from DRG tissue (L4-6) corresponding to the sciatic nerves. The mean grayscale density of autoradiogram signal bands was determined by averaging the values of image pixels corresponding to specific RNA-probe hybridizations. Preprotachykinin (PPT) mRNA levels were normalized to 28S rRNA levels as a measure of total RNA loaded. Cervical DRG tissue (C3-5) was used as an additional non-operated control. N=Non; B=Bupivacaine' L=Lumbar' C=Cervical.

Prolonged release of local anesthetic and polymer degradation near the sciatic nerve did not lead to differences in any of several biochemical comparisons made between the side that received PLAM implants and the contralateral control side, two weeks post-implantation (Table 1). There was no significant difference found in tests for: (1) acetylcholine receptor number in gastrocnemius muscle, (2) the level of substance P, a neuromodulator involved in nociception, in lumbar or cervical dorsal root ganglia, or (3) the level of RNA encoding for substance P, preprotachykinin (PPT), in lumbar dorsal root ganglia, using a novel small-sample Northern blot system, as demonstrated by FIG. 4.

TABLE 1

Biochemistry results of animals with PLAM implants, comparing the bupivacaine-treated leg to the contralateral control leg.

| Analysis | Control[a] | Bupivacaine-Treated[a] |
|---|---|---|
| Acetylcholine Receptor in gastrocnemius muscle (femtomole/mg protein) | 44.6 ± 1 | 3.3 ± 2.9* |
| Substance P content in DRG (femtomole/mg protein) | | |
| Lumbar (n = 7) | 0.12 ± 01 | 0.11 ± 01* |
| Cervical (n = 7) | 0.08 ± 01 | 0.07 ± 01* |

TABLE 1-continued

Biochemistry results of animals with PLAM implants, comparing the bupivacaine-treated leg to the contralateral control leg.

| Analysis | Control[a] | Bupivacaine-Treated[a] |
|---|---|---|
| Substance P mRNA in DRG (PPT/28S rRNA) | | |
| Lumbar (n = 5) | 1.04 ± 09 | 1.03 ± 05* |
| Cervical (n = 4) | 0.77 ± 10 | 0.87 ± 21* |

[a](Mean ± S.E.M.)
*p > 0.3, Bupivacaine-treated vs control

Plasma Levels

A potential risk of prolonged nerve blockade is systemic accumulation of local anesthetics, leading to convulsion, arrhythmia, and myocardial depression. To examine this risk, plasma concentrations of bupivacaine were measured in five additional rats implanted with Group 1 PLAM pellets (295±5 mg total), at 1, 4, 24, 48, 72 and 96 hours post-implantation. All concentrations were less than 0.1 µg/ml, far below the threshold for toxicity of 305 µg/ml.

In summary, prolonged reversible blockade of the rat sciatic nerve was achieved for periods of 2–6 days in vivo using release of bupivacaine from a bioerodable polymer matrix. The implants were well tolerated by the animals, and produced only mild inflammation consistent with the presence of a foreign body. Recovery of motor and sensory function appeared complete.

EXAMPLE 4

Implantation of PLAMs Containing Anesthetic in Combination with Antiiflammatory

Depending upon the method of preparation, it was common in the previous studies to observe some encapsulation around the PLAM at autopsy two weeks following implantation. Encapsulation involves formation of a fibrous material around foreign bodies. It begins with attempts by granulocytes to phagocytose and incorporate the foreign material during the initial acute inflammatory response. The process of encapsulation through fibrosis is due to histiocytes and fibroblasts, which generate the layers of collagenous connective tissue surrounding the implant. Encapsulation depends upon several factors, including the chemical and physical characteristics of the implant, the mechanical action of the implant, its site in the body and the presence of microorganisms.

The protective function which encapsulation provides may also produce unwanted scarring. An example of this is shown by the studies examining the presence of fibrous capsules around silicon breast implants. Besides forming a large "scar" inside the body, encapsulation may also be a limiting factor in the applicability and usefulness of biodegradable drug delivery systems. Work by Anderson, et al. (J. M. Anderson, H. Niven, J. Pelagalli, L. S. Olanoff, and R. D. Jones, "The role of the fibrous capsule in the function of implanted drug-polymer sustained released systems," J. Biomed. Mater. Res., 15, 889–902 (1981)) has shown that the fibrous capsule which eventually surrounds an implant retards the drug diffusion rate and consequently lowers the local and systemic drug levels. In addition, other studies have shown that the duration of sensory blockade in vivo with bupivacaine impregnated PLAM was less than that expected from the results of PLAMs examined in vitro.

A method which reduces encapsulation is therefore needed for two reasons: (1) to diminish the unwanted consequences of "scarring" and (2) to enhance the release behavior of drug-polymer sustained release systems.

In the present study, the effects of dexamethasone and cis-hydroxyproline on inflammation, encapsulation and duration of sensory and motor blockade following implantation of bupivacaine-impregnated polymer matrices along the sciatic nerves of rats have been determined. Each drug has been shown separately in other studies to act upon different components of the inflammatory process. (L. Christenson, L. Wahlberg, and P. Aebischer, "Mast cells and tissue reaction to intraperitoneally implanted polymer capsules," *J. Biomed. Mater. Res.*, 25, 1119–1131 (1991); L. Christenson, P. Aebischer, P. McMillian, and P. M. Galletti, "Tissue reaction to intraperitoneal polymer implants: species difference and effects of corticoid and doxorubicin," *J. Biomed. Mater. Res.*, 23, 705–718 (1989); D. Ingber and J. Folkman, "Inhibition of angiogenesis through modulation of collagen metabolism," *Lab. Invest.*, 59, 44–51 (1988); and J. P. Iannotti, T. C. Baradet, M. Tobin, A. Alavi, and M. Staum, "Synthesis and characterization of magnetically responsive albumin microspheres containing cis-hydroxyproline for scar inhibition," *Orthop. Res. Soc.*, 9, 432–444 (1991)). Their individual effects on reducing encapsulation and improving drug release behavior were examined in this study.

Methods and Materials

Implants

Copolymers of 1,3-bis(p-carboxy-phenoxy)propane and sebacic acid (20:80) were synthesized as described above. Polymers were repurified by three cycles of the following process:

Polymer was dissolved in chloroform, precipitated with 5 volumes of hexane, the solvents was removed, and the precipitate was washed with diethyl ether. Copolymers were then ground to a fine powder under liquid nitrogen, lyophilized overnight, and stored under $N_2$ at $-20°$ C. until use.

CHP PLAMs

PLAMs containing 10% and 20% L-cishydroxyproline (CHP) by weight of CPP:SA (20:80) copolymer were produced using the hot melt procedure, as follows:

Dry CHP is added to copolymer and mixed by both vortex and manual stirring with a spatula. The mixture is then transferred to a 1 cc syringe, heated for 10 to 15 minutes at $116°\pm2°$ C. until the polymer becomes molten but CHP remains solid with its crystals widely dispersed throughout the polymer. The mixture is then injected into Teflon® tubing. After the PLAM solidifies for 1 h, the PLAM in Teflon® tubing is cut into cylindrical pellets. The pellets are sterilized by gamma irradiation for 1 h and stored sealed at $-20°$ C. until use.

All CHP PLAMs were synthesized using Teflon® tubing ($3.1\pm0.2$ mm diameter, denoted "regular bore"). These pellets were cut 1 cm in length and weighed approximately 100 mg. Group 1 animals were implanted with one 10% CHP PLAM pellet on the experimental side. Group 2 animals were implanted with one 20% CHP PLAM pellet on the experimental side and another on the control side.

The protocols and results are shown in Table 3.

TABLE 3

Description of Groups.

| Group number | Experimental side | Control side |
|---|---|---|
| 1 | 1) 10% CHP PLAM<br>2) 20% bupivacaine PLAM | Sham |
| 2 | 1) 20% CHP PLAM<br>2) 20% bupivacaine PLAM | 20% CHP PLAM |
| 3a | 20% bupivacaine PLAM | Sham |
| 3b | 20% bupivacaine PLAM | Sham |
| 4 | bupivacaine PLAM | Control PLAM |
| 5 | ld-DMS/bupivacaine PLAM | Control PLAM |
| 6 | hd-DMS/bupivacaine PLAM | Sham |
| 7 | hd-DMS PLAM | Control PLAM |

Bupivacaine PLAMs

PLAMs containing 20% crystalline bupivacaine-HCL by weight of CPP:SA 20:80 copolymer were synthesized via the hot melt procedure described above for CHP PLAMs.

Two different-sized diameter Teflon® tubing were used: regular bore ($3.1\pm0.2$ mm) and large bore ($4.9\pm0.3$ mm). Regular bore pellets were cut 1 cm in length and weighed approximately 100 mg. Large bore pellets were cut 0.5 mm in length and weighed approximately 130 mg. Groups 1, 2 and 3a/3b animals were implanted with 3 regular bore bupivacaine pellets on the experimental side. Group 4 animals were implanted with 3 large bore bupivacaine pellets on the experimental side.

DMS/Bupivacaine PLAMs

PLAMs incorporated both bupivacaine and dexamethasone (DMS) were synthesized via the hot melt procedure described for CHP PLAMs with some differences in initial preparations.

A uniform mixture of DMS and bupivacaine was formed by combining DMS dissolved in 95% ethanol with bupivacaine dissolved in 95% ethanol. The solution was air-dried under the hood at room temperature until the ethanol evaporated and left behind a well-dispersed mixture of dry crystalline DMS and bupivacaine. The crystalline mixture was pulverized under mortar and pestle and combined with copolymer. The rest of the procedures followed those described for CHP PLAMs. All DMS/bupivacaine PLAMs were synthesized using large bore Teflon® tubing.

Two different dosage sets of DMS/bupivacaine PLAMs were produced: high dose (hd) DMS and low dose (ld) DMS. Hd-DMS/bupivacaine PLAMs contained approximately 60 µg DMS per pellet. Ld-DMS/bupivacaine PLAMs contained approximately 15 µg per pellet. Both sets contained 20% bupivacaine by weight. Group 5 animals were implanted with 3 hd-DMS/bupivacaine PLAM pellets on the experimental side. Group 6 animals were implanted with 3 ldDMS/bupivacaine PLAM pellets on the experimental side. The protocols and results are shown in Table 4.

TABLE 4

Classification of Capsules

| Group # | Type of Side | PLAM Type | No capsule | Diffuse capsule | Laminar capsule |
|---|---|---|---|---|---|
| 1 | experimental | 10% CHP + bup | | | 4 |
| 3b | experimental | bupivacaine | | | 4 |
| 4 | experimental | bupivacaine | | | 6 |
| 4 | control | control | | | 6 |
| 5 | control | control | | 1 | 4 |
| 7 | control | control | | 3 | 2 |
| 5 | experimental | ld-DMS/bup | 5 | | |

TABLE 4-continued

| | | | Classification of Capsules | | |
|---|---|---|---|---|---|
| Group # | Type of Side | PLAM Type | No capsule | Diffuse capsule | Laminar capsule |
| 6 | experimental | hd-DMS/bup | 5 | | |
| 7 | experimental | hd-DMS | 5 | | |

DMS PLAMs

PLAMs containing DMS were synthesized via the hot melt procedure described for CHP PLAMs with some differences in initial preparation, as follows.

A uniform mixture of DMS and copolymer was produced by combining DMS dissolved in chloroform with copolymer dissolved in chloroform. The mixture was air-dried under the hood at room temperature until the chloroform evaporated and left behind a dry well-dispersed mass of DMS and copolymer. The dry mixture was pulverized under mortar and pestle and transferred to syringe. The rest of the procedure followed those described for CHP PLAMs. All DMS PLAMs were synthesized using large bore Teflon® tubing. Group 7 animals were implanted with 3 DMS PLAM pellets on the experimental side.

Control PLAMs

Control PLAMs were synthesized via the hot melt procedure described for CHP PLAMs. Control PLAMs contained only CPP:SA (20:80) copolymer and all pellets were synthesized with large bore Teflon® tubing. Groups 6 and 7 animals were implanted with 3 control PLAM pellets on the control side.

In Vitro Release of Dexamethasone

Tritium labeled dexamethasone ($^3$H-DMS) was purchased from New England Nuclear Corporation (Boston, Mass.). An aliquot consisting of 107 counts was added to a mixture of 200 μg unlabelled DMS and 190 mg bupivacaine dissolved in 95% ethanol. This solution was air-dried under the hood at room temperature until the ethanol evaporated and left behind a well-dispersed mixture of dry crystalline $^3$H-labelled DMS, unlabelled DMS and bupivacaine. This dry crystalline mixture was pulverized under mortar and pestle and combined with 650 mg CPP:SA (20:80) copolymer. The rest of the procedure followed those described for CHP PLAMs. All $^3$H-DMS/unlabelled DMS/bupivacaine PLAMs were synthesized using large bore Teflon® tubing. Each pellet was placed in 5 mL of sterile 1X PBS (phosphate-buffered saline) containing 1% sodium azide and incubated at 37° C. The incubated 1X PBS media was removed and stored at −20° C., and replaced with 5 ml of fresh sterile 1×PBS at 2h, 6h and 24 h time points and then once daily thereafter for 3 weeks. The $^3$H released was counted using a liquid scintillation counter (Rackbeta 1214).

Behavioral Testing

Male Sprague-Dawley rats housed in groups of 4 were habituated to a hotplate of 56° C. both before and after surgery. They were tested between 10 am and 12 pm daily and allowed to adjust to their surroundings in a quiet room at 22°±1° C. for at least 30 minutes before testing. The rat was wrapped in a towel from the waist up for visual obstruction and hinderance of upper body motion. Held in the experimenter's hand, the animal's hindpaw was placed on the hotplate and latencies recorded, starting on contact and ceasing with withdrawal from hotplate, via a foot-switch connected to a computer. If latencies exceeded 12 seconds, the rat's hindpaw was removed to prevent injury. No rats were observed to have inflammation or blisters. Rats were tested for at least two weeks prior to surgery to achieve a consistent baseline latency, and testing continued for two weeks after surgery to confirm complete recovery from sensory blockade.

Motor blockade was rated on a 4-point scale. Animals with a motor block of 4 had a clubbed hindpaw and usually dragged their affected leg when walking. Motor block 3 animals walked normally but had toes that failed to splay when the animal was lifted. Animals with motor block of 2 showed toes that splayed but not as fully as normal or motor block 1 animals.

To better assess intensity of sensory block, hot plate latencies were subdivided into 4 classes: (1) maximum block intensity (MBI), when latency=12 sec, the maximum allowable time the rat's foot can remain on the hot plate before it is manually removed by the experimenter to prevent injury, (2) dense block, when latency=7–11, 3) partial block, when latency=4–7 sec, and 4) no block, when latency was less than 4 sec.

Surgery

All animals were anesthetized with 3.5%–4.0% halothane in oxygen and maintained with 1.5%–2.0% halothane. Anesthesia was achieved within 3–5 minutes post induction. Animals were tested by pinching of tailbase and pawpads to confirm the anesthetic state. The thigh area was shaved and an incision was made directly below the greater trochanter. The hamstrings were gently divided by blunt dissection to expose the sciatic nerve. PLAM pellets were placed adjacent to the sciatic nerve under direct vision in the fascial plane deep to the hamstrings and the site was irrigated with 0.5 cc of antibiotic solution (5000 units/mL penicillin G sodium and 5000 ug/mL streptomycin sulfate) to prevent infection. The most superficial facial layer was closed with a single suture. The edges of the outer skin were approximated and closed with one to two surgical staples.

For all rats, drug-containing PLAMS were implanted on the experimental side. The control (contralateral) side varied among the groups. Group 1 used 10% CHP PLAMs on the control side to compare the effects of bupivacaine and CHP PLAMs vs. CHP PLAMs alone. Groups 2, 3a/3b and 5 received sham operations on the control side to compare the effects of drug vs. both drug-free and PLAM-free states. Sham operations consisted of exposing the sciatic nerve, irrigation of the site with antibiotic solution, and closure of the surgical site without implantation of any PLAM pellets. Groups 4, 6 and 7 used control PLAMs on the control side to compare the effects of drug vs. drug-free PLAM states.

Necropsy

All groups, except groups 2 and 3a, were sacrificed at two weeks by $CO_2$ asphyxiation. Groups 2 and 3a were sacrificed five days post-surgery. Groups 4, 5 and 6 were given cardiac punctures and blood samples were taken for ACTH and cortisol assays. For autopsy, the skin of the dorsal thigh was removed. A midline transverse cut was made through each successive layer of hamstring muscle to locate the site of encapsulation, if any, and preserve its integrity and architecture. The capsule was excised by blunt dissection and placed in 10% formalin. A 3 cm segment of the sciatic nerve was removed from its exit point at the greater sciatic foramen to its branching point above the dorsal aspect of the knee joint. For light microscopy, a segment was fixed in 10% buffered formalin.

Statistics

All data were analyzed using repeated measure ANOVA, post-hoc paired t-tests, Fisher exact tests and Wilcoxon rank sum tests where deemed appropriate.

Histology

Nerves: For evaluation of sciatic nerves, cross-sections were processed, embedded in paraffin and sectioned at 2 μm and stained with hematoxylin eosin. 5–10 sections were studied via light microscopy by a pathologist in a blinded manner. Each cross-section was evaluated for (1) epineural inflammation, (2) epineural fibrosis, and (3) subperineural fibroblasts. Each parameter was rated on a severity scale of 0–4. A score of 0=no change, 1=mild, 2=moderate, 3=moderate-severe and 4=severe.

Capsules: Encapsulation was evaluated by gross examination at the time of dissection and through photographs by a blinded observer. This evaluation was divided into 3 categories. The first type was characterized by no true capsule. It involved nonspecific, unorganized inflammatory debris surrounding the implantation site. The other two capsule types were classified according to the manner of Ksander, et al. (G. A. Ksander, L. M. Vistnes and D. C. Fogerty, "Experimental effects on surrounding fibrous capsule formation from placing steroid in a silicone bag-gel prosthesis before implantation," *Plast & Reconstr. Surg.*, 62, 873–883 (1978)). The second type was characterized by flimsiness, an ability to be easily deformed and torn, and an irregular dull surface of white to gray color. This type was designated as a diffuse capsule. The third type was characterized by toughness, resistance to deformation by handling and tearing at excision, and a smooth glossy inner surface of yellowish-brown to clear translucence. This type was designated as a laminar capsule. It was a true histological capsule with highly organized, fibrous walls enclosing the implanted pellets, completely separating it from immediate surrounding tissue. A severity scale of 0–4, similar to that described above, was used to rank the degree of inflammation of the perineural fascia and muscle fascia.

Cross-sections of formalin-fixed capsules were examined by light microscopy and rated on a severity scale from 0–4, specifically looking at (1) thickness of capsule wall, (2) proportion of PMN's in relation to other inflammatory cells, (3) proportion of lymphocytes to other inflammatory cells, (4) proportion of plasma cells to other inflammatory cells, (5) proportion of foreign body giant cells to other inflammatory cells, (6) proportion of immature fibroblasts to mature fibroblasts, and (7) extent of collagen deposition in the capsule wall.

Results

In Vitro Release of DMS

The release of DMS from PLAM was nearly linear for the first 8 days and eventually reached a plateau by Day 21. Approximately 60% of DMS was released from PLAM by Days 7–8 and by Day 21, 97% of DMS was released (FIG. 1).

Histology

Capsules

Dexamethasone prevented capsule formation in all groups whose experimental side received DMS-containing PLAM pellets (Groups 5, 6, and 7). In contrast, CHP did not prevent encapsulation. [see Table 3] All groups treated with CHP (Groups 1 and 2) formed capsules around implants by the time of dissection. Groups implanted with bupivacaine PLAMs (Group 3b and 4) and no additive (DMS or CHP) developed capsules around implants. Groups which received control PLAMs (Groups 4, 5 and 7) also formed capsules around implants. DMS-treated sides were significantly different from contralateral control sides implanted with drug-free PLAMs (Group 5 and 7, p<0.0001). They were also statistically different from sides receiving CHP-(Group 1, p=0.0003) and/or bupivacaine-containing PLAM pellets (Group 3b and 4, p<0.0001). Capsules formed from drug-free PLAMs (control PLAMs) were histologically indistinguishable from those that resulted from drug-containing PLAMs (CHP and bupivacaine). This was determined through examination of a variety of inflammatory factors. Capsules produced from drug-containing PLAMs were statistically insignificant from drug-free PLAMs in terms of (1) capsule thickness, (2) acute PMNs, (3) foreign body cells, (4) collagen content, (5) immature fibroblasts, and (6) mature fibroblasts. Two categories produced marginal statistical significance (p=0.0461): chronic round cells and plasma cells. This implied that drug-containing PLAMs may produce slightly more inflammation of the chronic inflammatory type.

Nerves

All groups showed no statistical significance between experimental and control sides in all three inflammatory factors examined: (1) epineural inflammation, (2) epineural fibrosis, and (3) perineural fibroblasts. Comparisons of experimental sides receiving CHP and bupivacaine vs. bupivacaine alone (Group 1 versus Group 3b and Group 2 versus Group 3a) showed no statistical significance. No difference in neural inflammation was found comparing groups receiving 10% CHP vs. 20% CHP (Group 1 versus Group 2) and groups sacrificed Day 5 versus Day 14 (Group 3a versus 3b). Comparison of experimental sides receiving DMS/bupivacaine versus bupivacaine alone (Group 5 versus Group 4 and Group 6 versus Group 4) showed no difference. No difference was also found comparing groups implanted with bupivacaine alone versus DMS alone (Group 4 versus Group 7) and hd-DMS/bupivacaine vs. ld-DMS/bupivacaine (Group 5 versus Group 6). One set, Group 6 versus Group 7, showed statistical significance. Group 6 produced a greater degree of epineural inflammation (p=0.0238) than Group 7. The other two inflammatory factors, epineural fibrosis and perineural fibroblasts, were statistically insignificant for Group 6 versus Group 7.

Sensory and Motor Blockade Among Animals Treated with DMS and CHP

Figure 5:
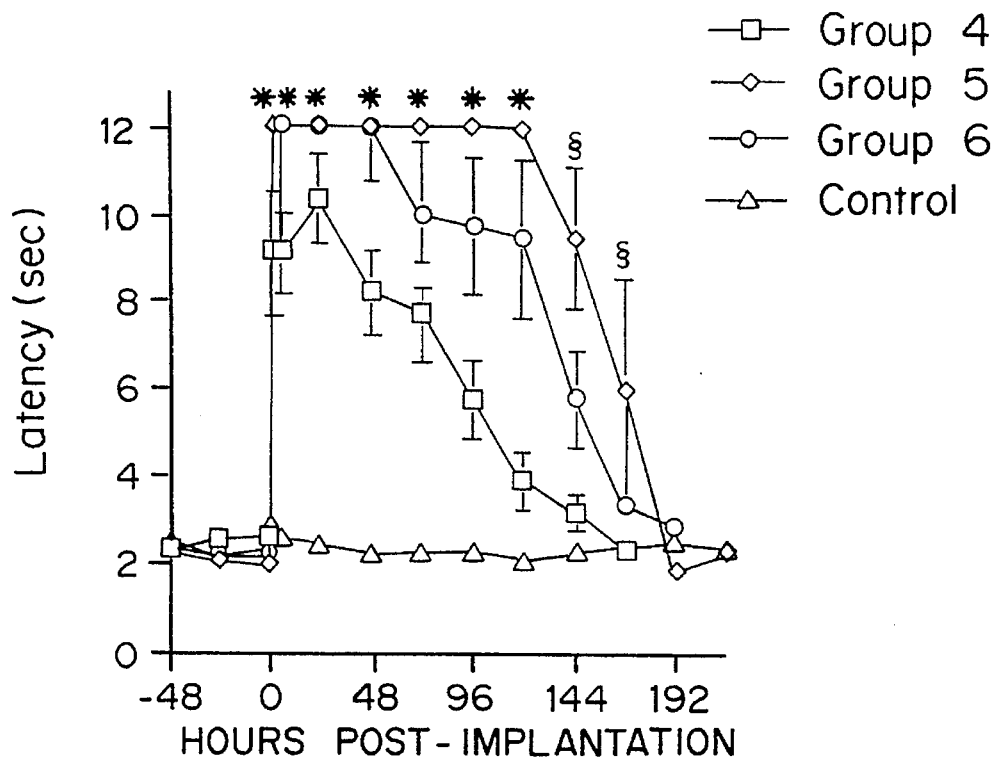
FIG. 5 is a graph of latency in seconds versus hours post-implantation for groups 4 (squares), 5 (diamonds), 6 (circles) and control (triangles) rats treated with PLAMs containing anesthetic and antiinflammatory.
Figure 6A:
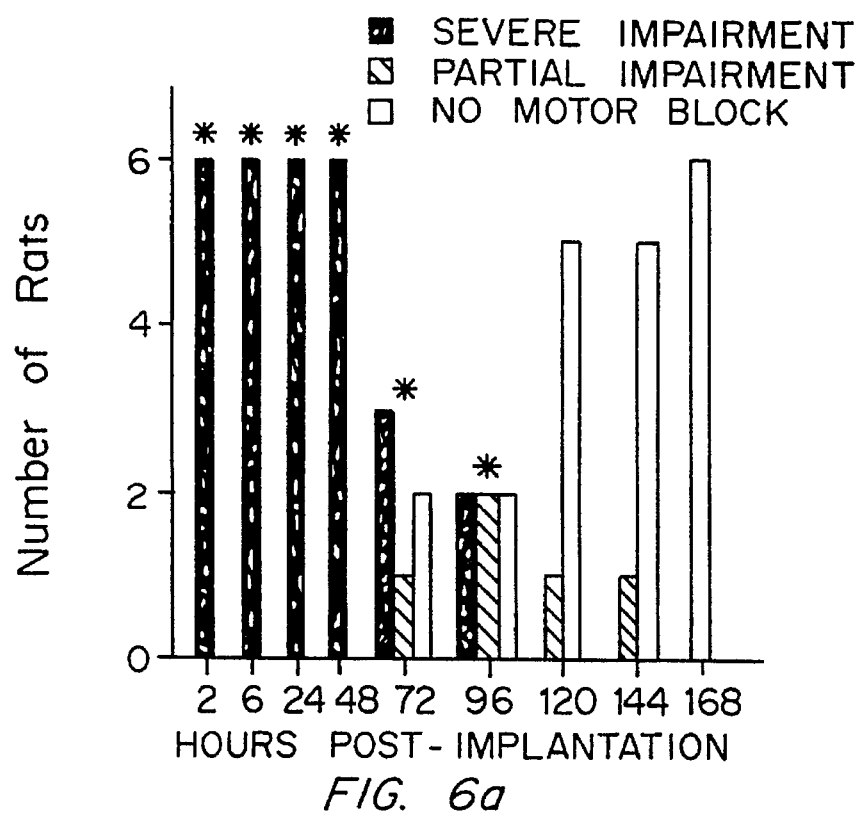
FIGS. 6a, b, and c are graphs of number of PLAM treated rats versus hours post-implantation who showed severe impairment (dark bars), partial impairment (stripes), and no motor block (open bars).
Figure 6B:
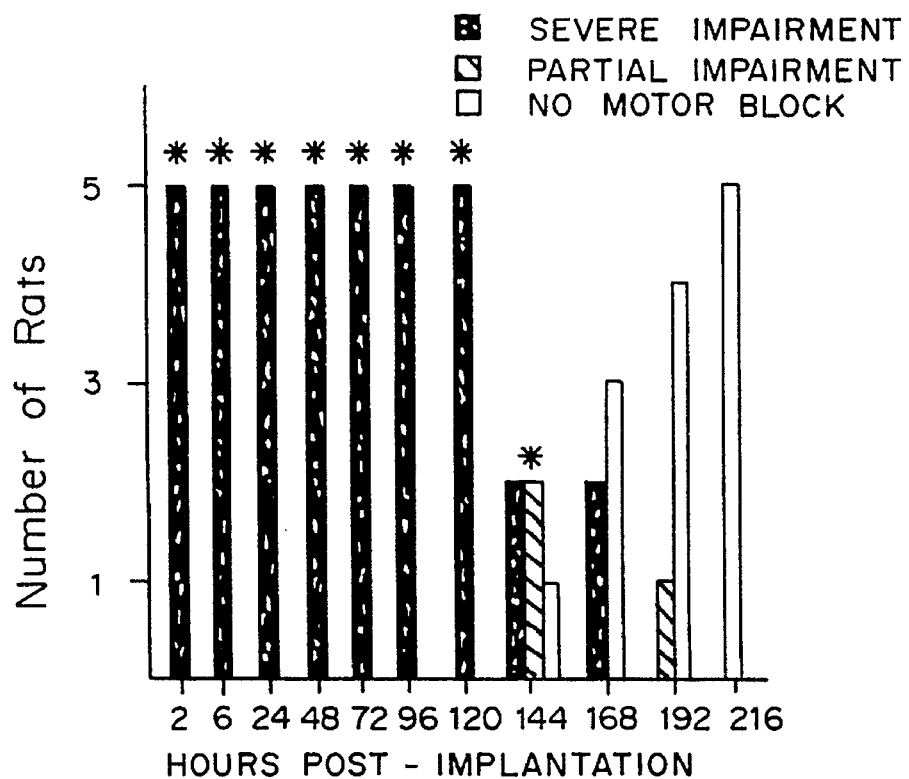

Group 5 (animals implanted with ld-DMS/bupivacaine PLAMs) had the longest sensory and motor blockade. Sensory blockage lasted for a period of 6–7 days with maximum block intensity (latency=12 sec) observed on days 1–5 in all animals, as shown by FIG. 5. Motor blockade lasted for 6–8 days with the densest motor block seen on day 1–5. All animals returned to baseline on Day 8, as shown by FIG. 6a.

Figure 6C:
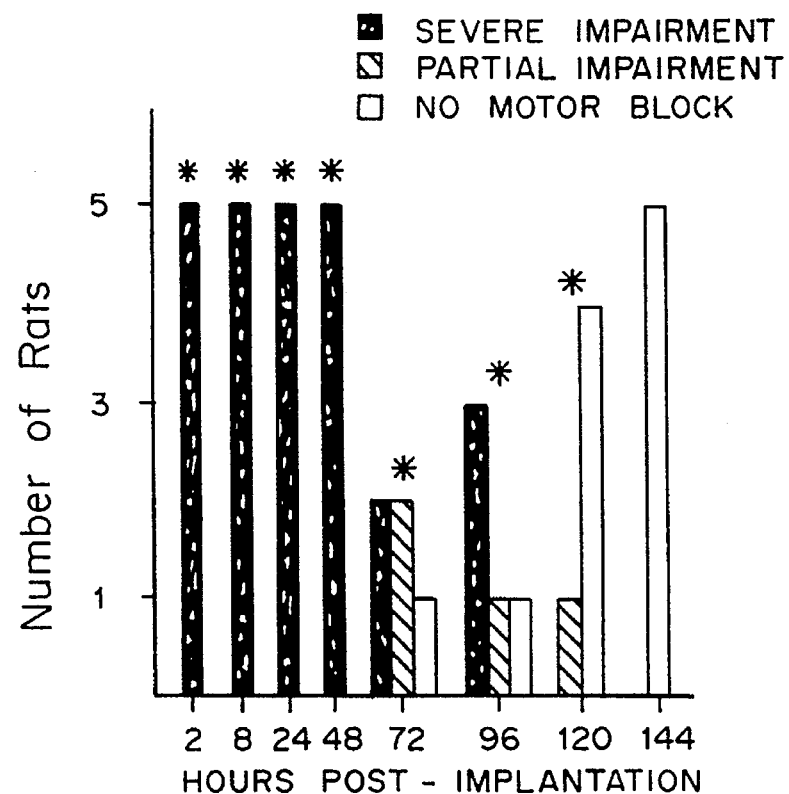

Rats implanted with hd-DMS/bupivacaine PLAMs (Group 6) also had sensory block lasting 6–7 days, as shown by FIG. 5. However, maximum block intensity was observed only on days 1–2 in all rats. A plateau of dense block (latency=7–11 sec) was seen on days 3–5. Motor blockade lasted for 3–5 days with the densest motor block occurring on day 1–2, as shown by FIG. 6c.

Group 4 animals (control group receiving large bore bupivacaine PLAMs) had sensory blockade lasting 5–6 days, as shown by FIG. 5. There were no time points when all animals had maximum block intensity simultaneously. However, dense sensory block (latency=7–11 sec) was observed on days 1–4 in all animals. Motor blockade lasted 3–6 days with densest block seen on Days 1–2, as shown by FIG. 6a.

Group 7 rats, who were implanted with hd-DMS PLAMs, showed no sensory and motor block, and all time points could not be distinguished from baseline.

Figure 7:
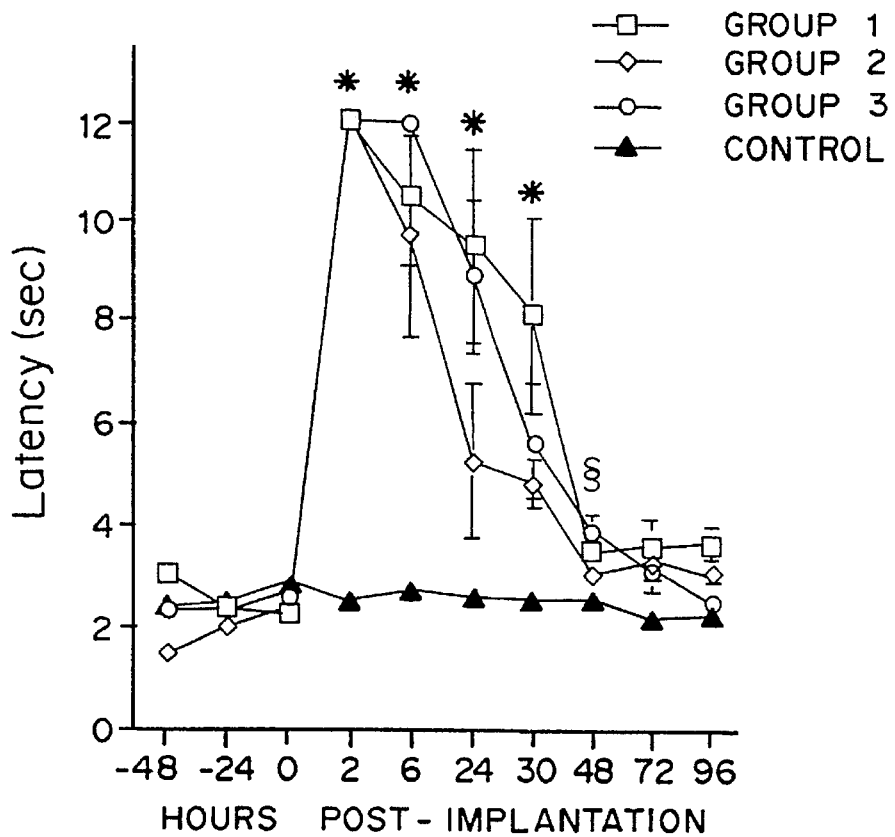
FIG. 7 are graphs of latency in seconds versus hours post-implantation for groups 1 (squares), 2 (diamonds), 3 (circles) and control (triangles) rats treated with PLAMs containing anesthetic and antiinflammatory.
Figure 8A:
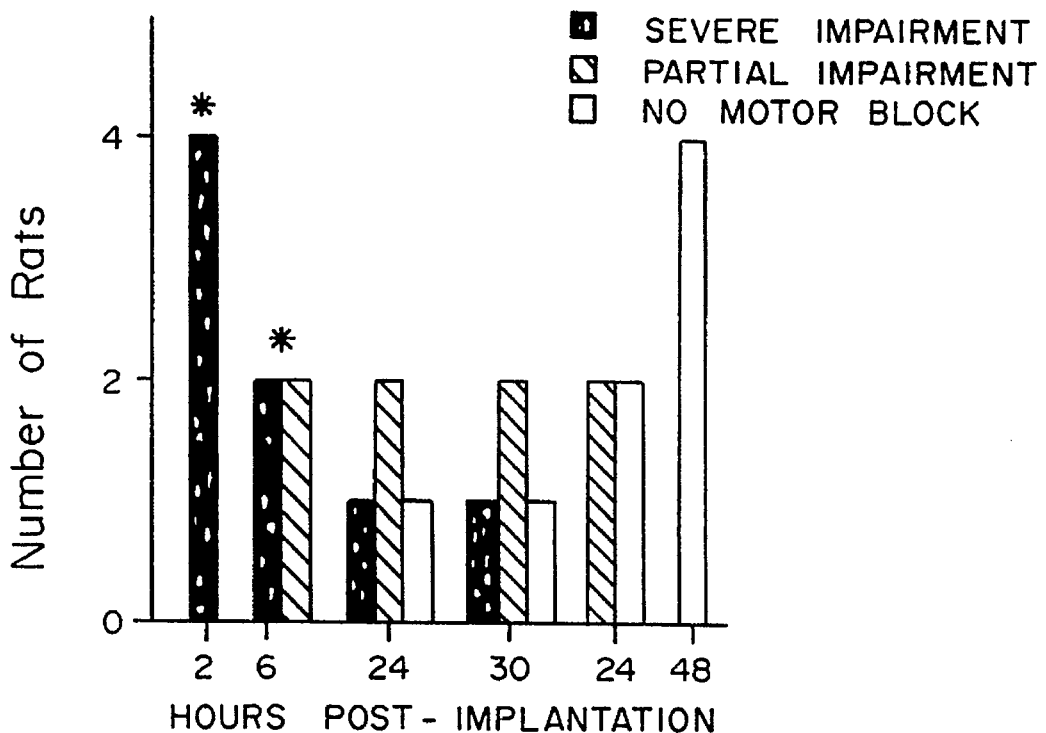
FIGS. 8a, 8b, and 8c are graphs of number of PLAM treated rats versus hours post-implantation who showed severe impairment (dark bars), partial impairment (stripes), and no motor block (open bars).
Figure 8B:
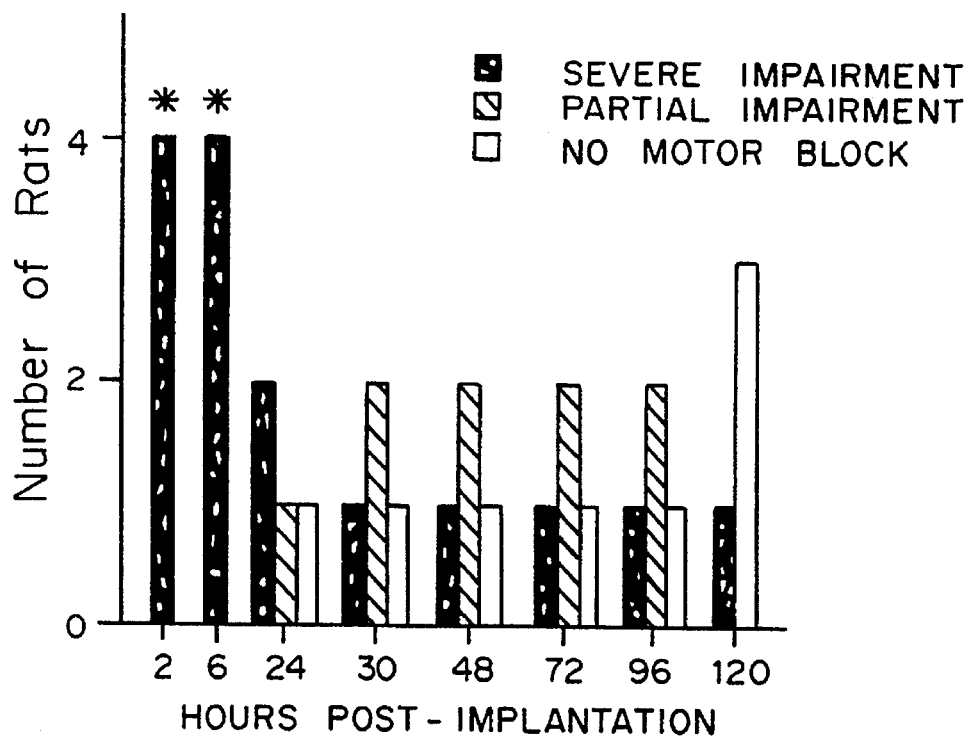
Figure 8C:
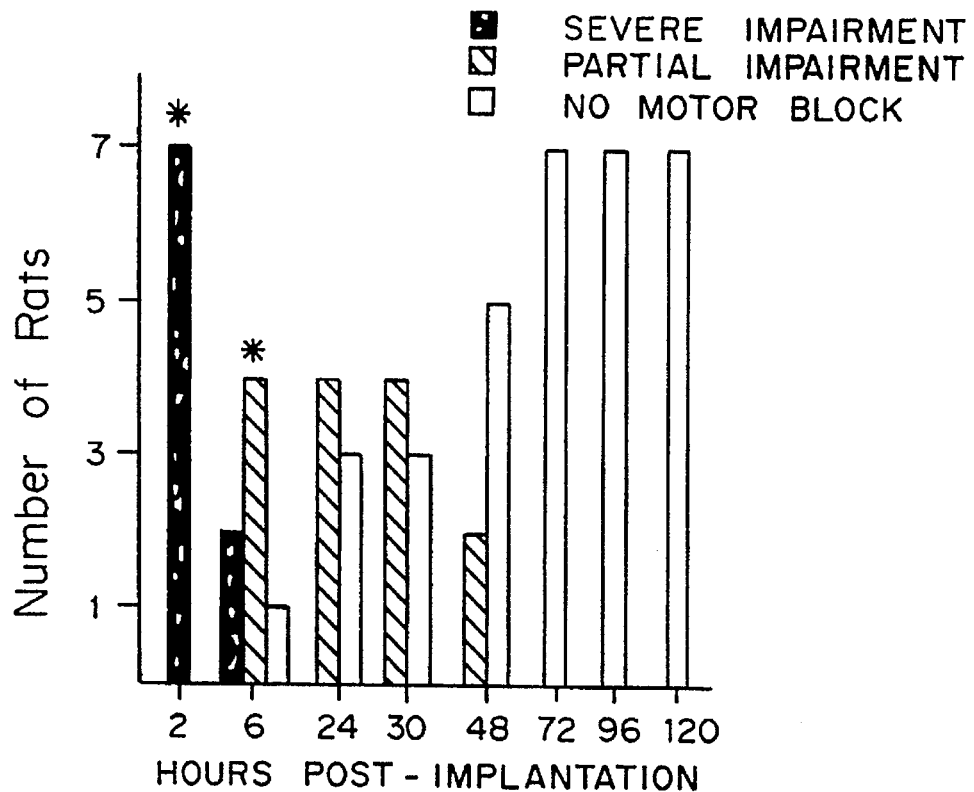

Group 1, 2 and 3a/3b rats, who were implanted with 10% CHP PLAM plus bupivacaine PLAMs, 20% CHP PLAMs and plus bupivacaine PLAMs, and bupivacaine PLAMs alone, respectively, all displayed similar sensory block durations and intensities. All groups showed sensory block durations of 2–4 days with dense block seen on Day 1 and the majority of rats returning to baseline on Days 2–4, as shown by FIG. 7. Motor blockade were similar for Groups 1 and 3a/3b. Duration of motor block lasted for 1–2 days with the densest block observed primarily on day 1. Group 2 had motor blockade lasting for 1–4 days with the densest block also occurring on day 1, as shown by FIGS. 8a, 8b and 8c. One animal from Group 2 was dropped from the study because it did not recover motor-and sensory-wise. One animal from Group 3a was dropped from the study because it did not recover motorwise, although its sensory functions were intact and it returned to baseline.

Plasma Assays for ACTH and Corticosterone

Plasma assays performed on Groups 5, 6 and 7 animals showed no difference in ACTH and corticosterone levels compared to normal values of rats taken at the same period of day and under similar stress-level conditions. Prolonged release of dexamethasone, approximately 5–10 µg per day for 2 weeks, did not cause pituitary suppression of ACTH and consequently, did not decrease plasma levels of corticosterone.

Summary of Results

The present study demonstrates that DMS released from biodegradable polymer matrices can prevent encapsulation around polymer implants seen during autopsy at 2 weeks post-implantation. Sensory and motor blockade is profoundly enhanced in animals treated with DMS. Light microscopy studies show that DMS-treated sides have equivalent neural inflammation to sham operations, control PLAMs or bupivacaine PLAMs.

Modifications- and variations of the present invention, a biodegradable controlled release device for the prolonged and constant delivery of a local anesthetic agent, will be apparent to those skilled in the art from the foregoing detailed description of the invention. Such modifications and variations are intended to come within the scope of the appended claims.

We claim:

1. A method for sustained local anesthesia or regional nerve blockade at a site in a patient, the improvement comprising administering by injection into tissue a local anesthetic incorporated into microparticles formed of a biocompatible polymer degrading at least fifty percent in less than six months following injection into the patient which is selected from the group consisting of polyanhydrides, copolymers of lactic acid and glycolic acid, poly(glycolic acid), polyorthoesters, proteins, and polysaccharides, wherein the local anesthetic is uniformly incorporated into the microparticles in a concentration effective to achieve sustained release of anesthetic at the site for at least three days following injection of the microparticles.

2. The method of claim 1 wherein the microparticles are selected from the group consisting of microspheres and microcapsules.

3. The method of claim 1 wherein the local anesthetic is selected from the group consisting of bupivacaine, dibucaine, etidocaine, tetracaine, lidocaine, xylocaine and salts thereof.

4. The method of claim 1 wherein the local anesthetic is incorporated into the microparticles at a percent loading of between 0.1% and 70% by weight.

5. The method of claim 1 wherein the microparticles are made using a hot melt process.

6. The method of claim 1 wherein the polymer does not elicit inflammation following injection of the microparticles into a patient.

7. The method of claim 2 further comprising administering the microparticles in combination with a pharmaceutically acceptable carrier by injection.

* * * * *